(12) United States Patent
Kopanic et al.

(10) Patent No.: US 7,182,739 B2
(45) Date of Patent: Feb. 27, 2007

(54) THERAPY PATCH

(75) Inventors: Robert J. Kopanic, Racine, WI (US); Daniel G. Lee, Milwaukee, WI (US); Pamela J. Taylor, Mount Pleasant, WI (US); Jeffrey L. Harwig, New Berlin, WI (US); Lawrence J. Fenske, Madison, WI (US); Evan A. Sparks, Madison, WI (US); Miles William Noel Hember, Cambridge (GB); Charles F. Kilby, St. Neots (GB); Jaime R. Allen, Milwaukee, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 0 days.

(21) Appl. No.: 11/127,493

(22) Filed: May 12, 2005

(65) Prior Publication Data

US 2006/0258962 A1    Nov. 16, 2006

(51) Int. Cl.
*A61H 1/00* (2006.01)

(52) U.S. Cl. ............ 601/15; 601/49; 601/57; 601/70

(58) Field of Classification Search ............ 601/15, 601/46, 57–58, 60, 64, 67, 69, 70–71, 79, 601/148, 49; 600/15; 607/97, 108, 109, 607/111, 112
See application file for complete search history.

(56) References Cited

U.S. PATENT DOCUMENTS

| | | |
|---|---|---|
| 3,664,332 A | 5/1972 | Vecchio |
| 3,727,607 A | 4/1973 | Dill |
| 3,885,553 A | 5/1975 | Vecchio |
| 4,559,047 A | 12/1985 | Kapralis |
| 4,574,787 A | 3/1986 | Jacobs |
| 4,592,358 A | 6/1986 | Westplate |
| 4,607,624 A | 8/1986 | Jefferson |
| 4,700,706 A | 10/1987 | Munch |
| 4,925,743 A | 5/1990 | Ikeda et al. |
| 4,979,502 A | 12/1990 | Hunt |
| 5,072,724 A | 12/1991 | Marcus |
| 5,205,278 A | 4/1993 | Wang |
| 5,327,886 A | 7/1994 | Chiu |
| 5,342,412 A | 8/1994 | Ueki |
| 5,415,624 A * | 5/1995 | Williams .............. 602/21 |
| 5,423,874 A * | 6/1995 | D'Alerta .............. 607/72 |
| 5,577,273 A | 11/1996 | Newkirk et al. |
| 5,704,902 A | 1/1998 | Vandenbelt et al. |
| 5,797,859 A | 8/1998 | Prehodka |
| 5,902,256 A * | 5/1999 | Benaron .............. 601/15 |
| 5,918,590 A | 7/1999 | Burkett et al. |

(Continued)

FOREIGN PATENT DOCUMENTS

GB    2.378.388    2/2003

*Primary Examiner*—Michael A. Brown

(57) ABSTRACT

Therapy patches are disclosed which are designed to deliver vibration and heat (or cold) to human skin so as to provide muscle relief. These patches have a chemical pouch that generates heat or cold upon initiation. They also have a motor and battery to provide a vibration source. Forms of the invention have an adhesive so that the patch can be attached to the skin (and thus need not be manually held in place during use). Kits are also provided in which the motor and battery can be used with a string of linked, severable replacement pouches. Methods of using these patches are also disclosed.

19 Claims, 7 Drawing Sheets

U.S. PATENT DOCUMENTS

| | | |
|---|---|---|
| 5,984,995 A | 11/1999 | White |
| 6,099,556 A | 8/2000 | Usui |
| 6,155,995 A | 12/2000 | Lin |
| 6,203,509 B1 | 3/2001 | Duboff |
| 6,322,532 B1 | 11/2001 | D'Sa et al. |
| 6,336,935 B1 | 1/2002 | Davis et al. |
| 6,511,446 B1 | 1/2003 | Wu |
| 6,908,448 B2 | 6/2005 | Redding, Jr. |
| 2003/0056281 A1 | 3/2003 | Hasegawa |
| 2003/0116452 A1* | 6/2003 | Saric et al. ............... 206/219 |
| 2004/0091663 A1 | 5/2004 | Jang |
| 2004/0143199 A1 | 7/2004 | Cotterell-Grant et al. |
| 2004/0228803 A1 | 11/2004 | Smith et al. |
| 2004/0244412 A1* | 12/2004 | Trinh et al. ............... 62/530 |
| 2005/0059909 A1 | 3/2005 | Burgess |
| 2005/0075592 A1* | 4/2005 | Garon ............................ 602/2 |
| 2005/0234516 A1* | 10/2005 | Gueret ........................... 607/3 |
| 2006/0015059 A1 | 1/2006 | Redding, Jr. |

* cited by examiner

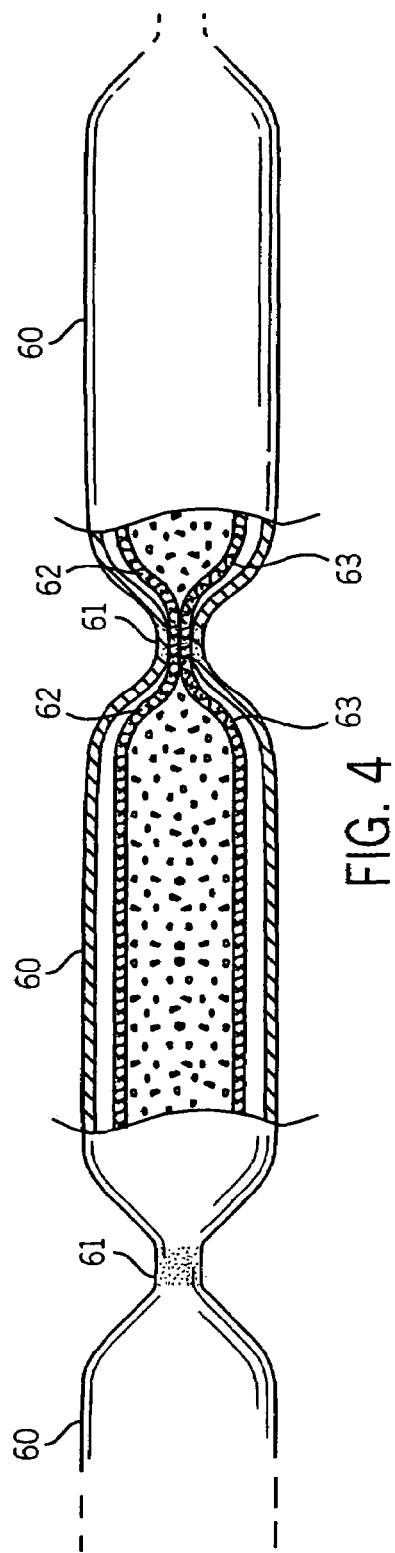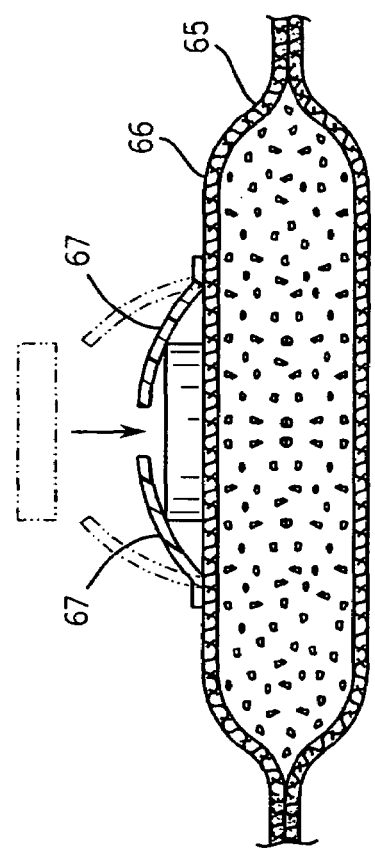

84

85

THERAPY PATCH

CROSS-REFERENCE TO RELATED APPLICATIONS

Not applicable

STATEMENT REGARDING FEDERALLY SPONSORED RESEARCH/DEVELOPMENT

Not applicable

BACKGROUND OF THE INVENTION

The present invention relates to therapy patches, and in particular to patches configured to apply heat or cold, along with vibration, to desired external areas of the body. "Therapy" is defined herein to include treatments to relax or otherwise provide a beneficial sensation, such as for example to treat sore muscles and the like. These devices are particularly useful for treating human muscle pain by externally applying the heat and vibration to a skin area.

A variety of electrical heating pads are known for treating muscle pain. They are typically linked to a power cord that plugs into a wall outlet. Some of these devices also incorporate a vibration system to enhance the effect of the applied heat. Where a power cord is required the device is not useful at locations where there is no nearby electrical plug. Apart from this problem, a consumer may also find it undesirable to have a linked power cord nearby. For example, if the consumer wishes to apply the pad while they sleep they may be concerned about getting tangled in the cord should they roll over.

Other types of known heating/vibratory devices use a battery to power the heater and/or vibrator. See e.g., U.S. Pat. Nos. 4,607,624, 4,979,502, 5,327,886, and U.S. Pat. No. 6,511,446. However, these devices required a large or overly expensive battery for typically desired periods of operation.

U.S. Pat. No. 5,902,256 disclosed an electrically driven vibrating massage unit. In this patent there was a heat (or cold) source that did not require a drain on the electrical power supply for the vibrating unit. Instead, heat or cold sinks were heated (or cooled) using a separate power supply, and the sinks were then inserted into the device. This system had the disadvantage of requiring a separate station for modifying the temperature of the heat or cold sinks.

There are also other known devices which have a pouch or other small structure that contains chemicals that react exothermically (upon initiation) to expel heat. See e.g. U.S. Pat. Nos. 4,925,743, 5,205,278 and U.S. Pat. No. 5,342,412. These devices can then be directed against sore tissue or muscle as desired by the user, or even more typically be inserted into a glove or boot to provide prolonged protection from extreme cold conditions. However, these devices did not address the desirability of associating a portable vibratory system with the heating source, much less solve the weight and power concerns that such a structure would have.

In connection with designing devices of this type, apart from the problems noted above, there are additional problems with ensuring that the vibration that is produced by the device is used in an efficient manner that extends to the full contact surface of the device. Some known devices have regions of high vibration and other portions of their contact surface with insufficient vibration. This problem makes such devices difficult to design as the size of the contact surface grows.

Thus, it can be seen that a need exists for improved, lightweight, inexpensive, self-contained vibrating heating/cooling pads.

BRIEF SUMMARY OF THE INVENTION

In one aspect the invention provides a therapy patch configured to deliver either heat or cold, together with vibration, to a target skin location on an animal (preferably human) body. The therapy patch has a pouch defining a cavity that contains an active configured to chemically generate heat or cold upon initiation. There is also a motor so associated with the pouch so as to cause the pouch to vibrate when the motor is operating. There is also a means for attaching a battery to the motor, and preferably also such a battery.

In preferred forms the pouch defines a frame surrounding an essentially central mounting position, and the motor is mounted in the mounting position. Vibrations produced by the motor spread throughout the device.

The frame can be substantially annular and the essentially central mounting portion can be a recess defined by the frame. The motor can then be in the form of a puck that is retained between the mounting portion of the pouch and an outer cover extending over that mounting portion and connected to the frame. The cover encloses an opening sized to enable removal and installation of the motor.

The active may comprise iron powder, and the pouch may be in the form of a bag having a porous side wall portion that can allow ambient air to flow to the active when the porous side wall portion is exposed to ambient air. A first strip may cover the porous side wall portion to achieve this when the first strip is peeled-off.

The active may instead be other chemical(s) that can achieve an exothermic reaction. For example, the active may be a gel containing sodium acetate which is positioned in the pouch. A disc initiator can be actuated to induce a force in the gel to initiate an exothermic reaction.

Alternatively, the chemistry may be such so as to cause an endothermic reaction resulting in cooling. For example, the dissolving of ammonium nitrate crystals in water that has been released from a frangible ampoule is a known chemistry that once initiated will create a cooling pouch.

There can also be an adhesive layer attached to the pouch and a second strip that removably covers the adhesive layer. When the second strip is removed from the adhesive layer the adhesive layer is configured to be suitable to attach the pouch to human skin (e.g. against the back of a neck). Alternatively, there can be a skin interface layer connected to the pouch having a flocked exposed surface.

The motor may be controlled by providing it with a pair of exposed electrical terminals separated by a nonconductive tab. The tab can be movable between a first position in which the tab separates the terminals and a second position in which the tab is removed from the terminals to bring the terminals in contact with each other and activate the motor (e.g. the terminals are biased towards each other). Alternatively, the motor can have a switch configured to be depressed to activate and deactivate the motor.

Other on/off devices for controlling a motor are also suitable to control the motors of the present invention. For example, there may be a computer controller that can repetitively activate and deactivate the motor to create a pulsing sensation at a single locus. Alternatively, the controller can alter the speed of the motor and thus the amount of vibration in a defined way (e.g. a slow "warm up" speed, followed by a vigorous fast primary speed, followed by a slower "cool down" speed).

In another aspect the invention provides a muscle relief kit configurable to deliver heat (or cold) and vibration to a target skin location on an animal (preferably human) body. The kit includes a motor capable of causing vibrations when the motor is operating, means for attaching a battery to the motor, and at least two patches (preferably a string of up to ten of such patches). Each patch has a pouch defining a cavity that contains an active configured to chemically generate either heat or cold upon initiation, and each patch has a mounting location for mounting the motor. A battery is also preferably provided with the kit.

The patches are provided in the kit in a form where they are connected along a tearable linking web. The linking web is sealed such that even when a first patch is separated from an adjacent patch by tearing through the linking web between them, the tearing through the linking web can be achieved without exposing the interior of the adjacent pouch to ambient air.

In another aspect the invention provides a method for applying heat or cold, in addition to vibration, to human skin. The method involves obtaining a therapy patch of the above type and then initiating the active so as to chemically generate heat or cold. One activates the motor so as to cause the patch to vibrate, and contacts human skin with the patch while it is vibrating and generating heat or cold. The contacting step may involve sticking the patch onto the human skin through the use of an adhesive adhering to the pouch and the skin. One can then remove the device from the skin, remove the motor and battery from the patch, and use the motor (and possibly also the battery) with another patch. Thus, the motor and battery do not have to be thrown away before their useful life is exhausted.

Because the motor can be essentially centrally located in preferred embodiments, its vibration effects can be optimally spread out throughout the patch. Hence, the size of the patch can be relatively large for a given desired maximum weight. Note that if the patch were rectangular the "central" area would be defined as a region adjacent to a point defined by lines crossing from the opposite diagonals of the rectangle.

Because the battery for these devices need not be used to generate the heat or cold, it can be kept relatively small in size for any given desired life of operation. As the device is lightweight, the device can be affixed to the skin and left in place without the need for a human to continue to hold the device in place. Moreover, the small size of the battery and motor permits peripheral portions of the patch to be able to bend in shape, following the contours of the human body. This improves temperature transfer characteristics as one can avoid gaps between the patch bottom surface and the skin near the periphery of the device. Further, because the motor (and an incompletely used battery) can be moved to the next patch once the first patch chemistry is exhausted, the cost of using the device is kept low.

The foregoing and other advantages of the present invention will be apparent from the following description. In the description reference is made to the accompanying drawings which form a part thereof, and in which there is shown by way of illustration, and not limitation, preferred embodiments of the invention. Such embodiments do not necessarily represent the full scope of the invention, and reference should therefore be made to the claims herein for interpreting the scope of the invention.

BRIEF DESCRIPTION OF THE DRAWINGS

FIG. 3 is a sectional view taken along line 3—3 of FIG. 1, but with an exposed initiator system also added;

FIG. 4 is a side elevational view, partially broken away, of a series of connected therapy patches, the series being suitable for use as part of a preferred kit of the present invention;

FIG. 5 is a sectional view of an alternative therapy patch of the present invention;

DETAILED DESCRIPTION OF THE PREFERRED EMBODIMENTS

Figure 1:
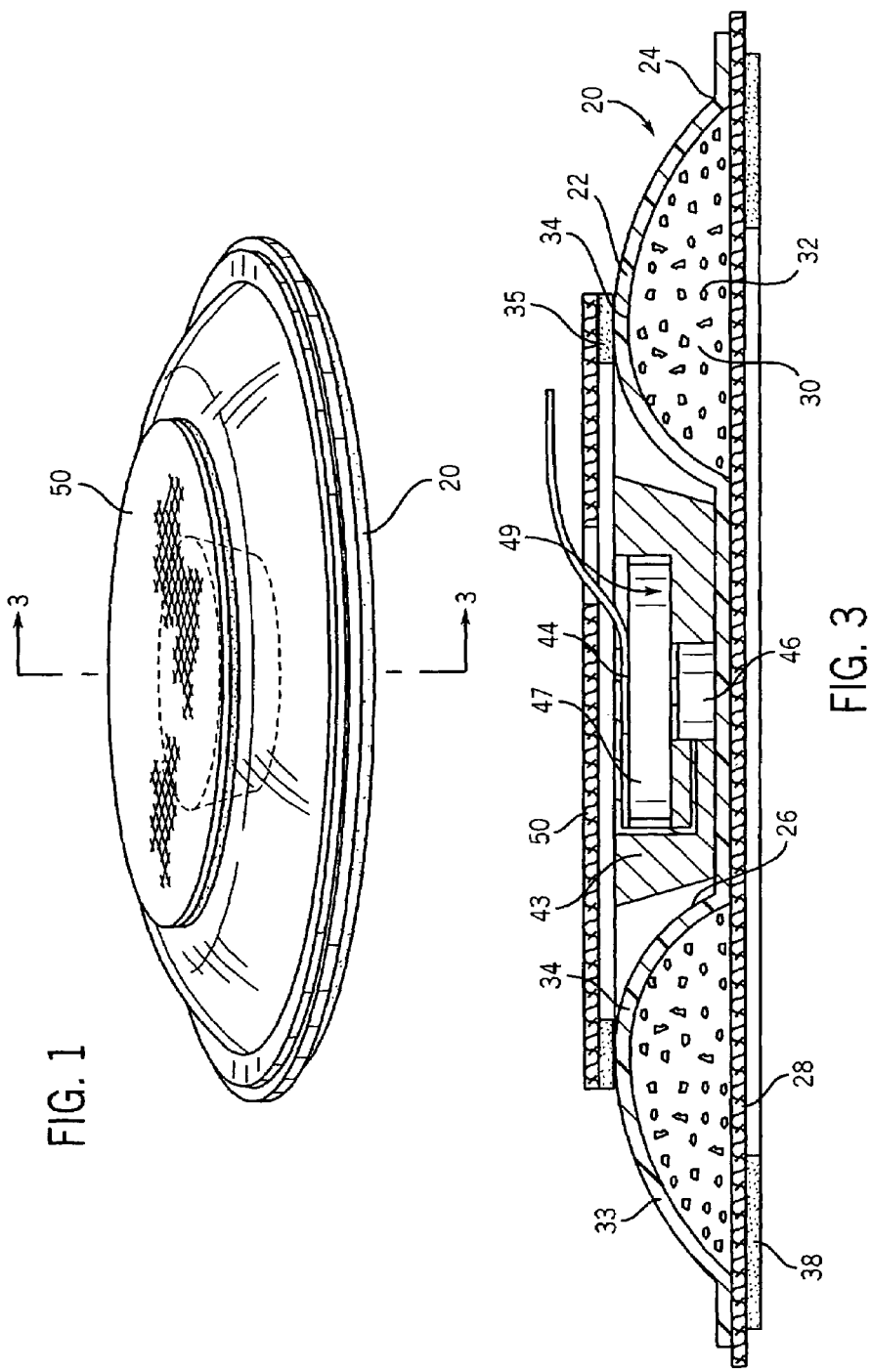
FIG. 1 is a frontal, top perspective view of a preferred therapy patch of the present invention.
Figure 2:
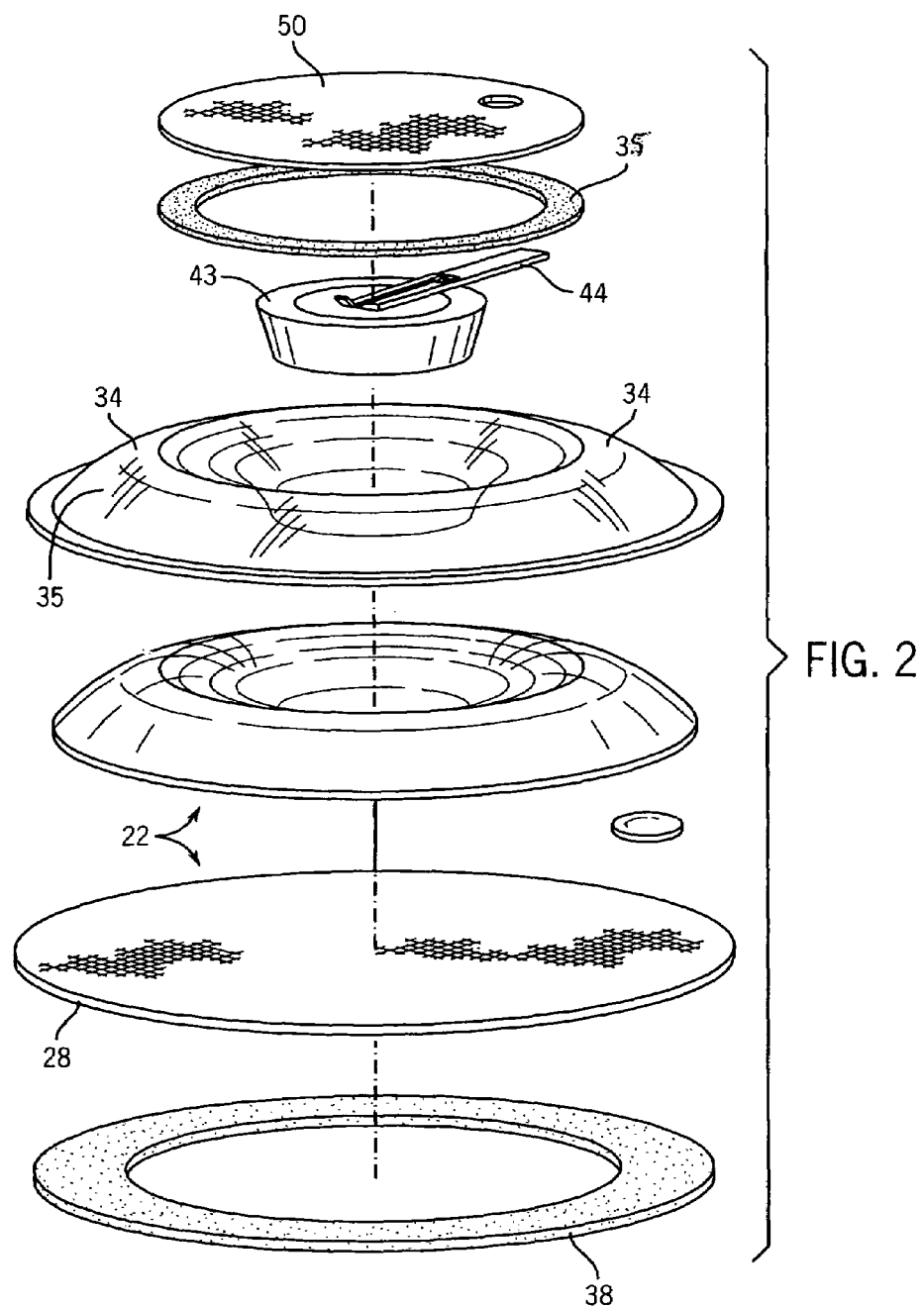
FIG. 2 is an exploded perspective view thereof.

Referring to FIGS. 1–3, a therapy patch 20 is disclosed that can be adhered to a human skin surface. This patch 20 can be designed to deliver either heat or cold, as well as vibration. It has a pouch 22 having a substantially annular periphery 24 that surrounds a centrally disposed recess 26. Periphery 24 and recess 26 are both supported by a flat base 28.

Periphery 24 defines an internal void 30 that contains an active 32 which can be formed from a chemical or mixture of chemicals capable of emitting heat or cold upon initiation in response to an occurrence of a predetermined condition (e.g., by way of an exothermic or endothermic internal reaction). For example, a well-known type of heating pouch for insertion in gloves and boots uses iron powder, a small amount of water, vermiculite, active carbon, and sodium chloride inside a pouch. When ambient air reaches the iron, it oxidizes, giving off heat. Alternatively, dissolving of ammonium nitrate crystals into water to create cooling, the water being contained within a frangible bag or ampoule that is broken open to release the water into the ammonium nitrate crystals, will begin an endothermic reaction.

The mixture just referred to of iron powder, water, vermiculite, active carbon, and sodium chloride can, as one example, constitute the active 32 in the present invention. Then, at least a portion of wall 33 can be, or can be made, porous so as to selectively allow ambient air to reach internal void 30. Where the entire wall 33 is air permeable, the patch would normally be stored in an airtight pouch prior to use. Alternatively, and as shown, only a portion of the wall 34 immediately adjacent the removable ring/first strip 35 could be air permeable. Upon removal of the ring/first strip 35, the air permeable portion of the wall 34 is exposed to air.

An adhesive ring 38 covers a portion of the flat base 28 and is suitable to stick on both the bottom of the flat base 28 and human skin. If desired, the bottom surface of ring 38 and/or of the base 28 can be covered with a flocked material to increase comfort of the consumer. If desired, there can be an additional peel-off backing/second strip (not shown) covering the bottom surface of ring 38 prior to use.

Recess 26 is sized to receive a resin casing 43. It mounts a puck 49 having a battery 47, an initiator 44 and a motor 46, the latter having a vibrating attribute. In this regard, the motor 46 can have an internal off-center weight that rotates during operation (under self-contained battery power) to induce vibrations in the pouch 22 that are communicated to the target tissue when therapy patch 20 is attached to the skin surface. The motor 46 and/or battery 47 can be designed for use with a first and then one or more subsequent therapy patches 20, or can be designed for use with only an original therapy patch, to be disposed of when the patch is thrown away.

Figure 9:
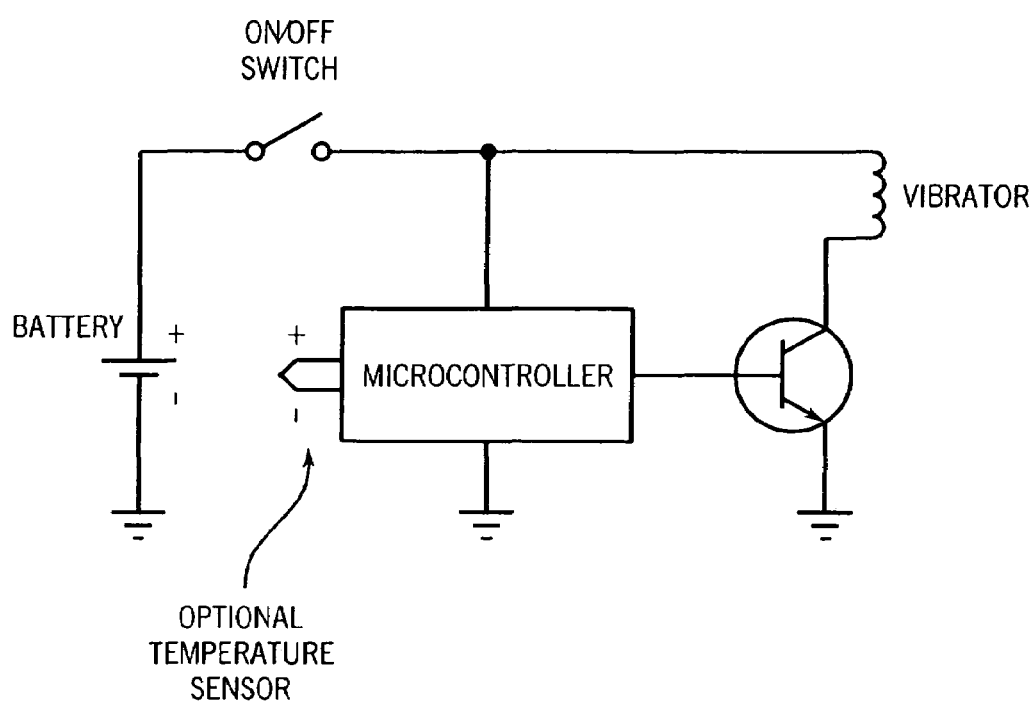
FIG. 9 is a circuit diagram showing possible control circuitry for an embodiment of the present invention.

The motor 46 can be arranged simply to be on or off. However, as noted above, it is also possible to control the motor 46 via a microcontroller to produce random or controlled pulsed on/off cycles. Microcontrollers capable of providing this feature are available from such companies as the Atmel Corporation. By including a thermistor, diode or other temperature sensor in the patch 20, it would also be possible to control motor activity in relation to the temperature of the patch, for example starting the motor 46 only once the patch's preferred operational minimum temperature has been reached, and stopping the motor as the temperature begins to move sufficiently back toward ambient temperatures. An example of possible circuitry to accomplish this is shown in FIG. 9.

Cover 50 is provided which can be formed from a flocked PVC that spans over the motor 46 and battery 47, and is connected to wall 34 via the adhesive ring 35. It will thus be appreciated that the periphery of the recess 26, and the cover 50 cumulatively provide a casing that encapsulates motor 46.

To begin a chemical reaction an air permeable portion of the wall 33 can be exposed to air (e.g. the cover 50 and associated ring/strip 35 can be removed). To start motor operation as shown in FIG. 3, the pull tab initiator 44 can be removed, thereby permitting an upper contact of the motor 46 to bias down onto the battery 47. In another aspect (not shown), the initiator 44 could be in the form of a switch that provides tactile feedback when depressed. When the motor is switched on, this will initiate vibration.

In FIG. 4 there is shown a string of patches 60 which are linked together (e.g. analogous to a roll of kitchen paper towels). These patches 60 are rectangular in top view and have a selected cavity, motor, and battery arrangement of the sort described above (e.g. possibly analogous to the FIG. 1 construction, or alternatively as shown in FIG. 5 on an outer surface). A feature of particular interest with respect to FIG. 4 is that these patches are now linked together via web sections 61 and thus may provide a refill supply. Alternatively, a series of linked patches can be used as a group, with multiple motors and batteries, to affect a more extended area on the body.

When linked patches are used as a group, with multiple motors and batteries, the motors may be allowed to run independently. Alternatively, they may be so governed as to operate in a coordinated way. As an example, if the motors in a connected series of patches are made to pulse in succession down the series, the effect could be a sensation of kneading, rolling, or pulsing motions across the body. A microcontroller (similar to that discussed, above, with respect to pulsing operation of a single patch) could be programmed to coordinate the activation of such a series of motors. Alternatively, most motors could be controlled to work continuously, while a particular motor (or motors) could be provided with special pulsing instructions. This might be a system suitable for focusing on a particular area of ache, while also more generally providing massaging and heat.

When patches are to be used individually, one can, for example sever a patch 60 off of the string along a web section 61. Because the pouch walls 62 and 63 are sealed together in this region, the severing will not expose the inner pouch of the adjacent patch to air. Thus, this provides a unique refill supply. When the chemicals in a first patch 60 are exhausted, the motor and battery can be removed from that patch and positioned in the next patch that is torn off. However, the tearing process does not compromise the patches that are not to be immediately used.

In FIG. 5 an alternative patch 65 is depicted. In this construction, rather than the motor being mounted in a recess in the pouch, it is mounted on an upper surface 66 of the pouch by having spring arms 67 clamp the motor down in a removable fashion. Thus, the mounting position for the motor is not limited to insertion in a recess. While insertion in a recess may help transmit vibration, it also exposes the motor and the battery to greater heat or cold, thereby possibly reducing the life of either or both. Thus, the FIG. 5 construction may have advantages in certain contexts.

There are other possible alternatives for mounting the motor. Rather than having a permanent recess, or a permanent set of tabs, one might construct the pouch so that it automatically closes around the motor and battery once they are positioned in the pouch, somewhat like a foldable coin purse.

Figure 6:
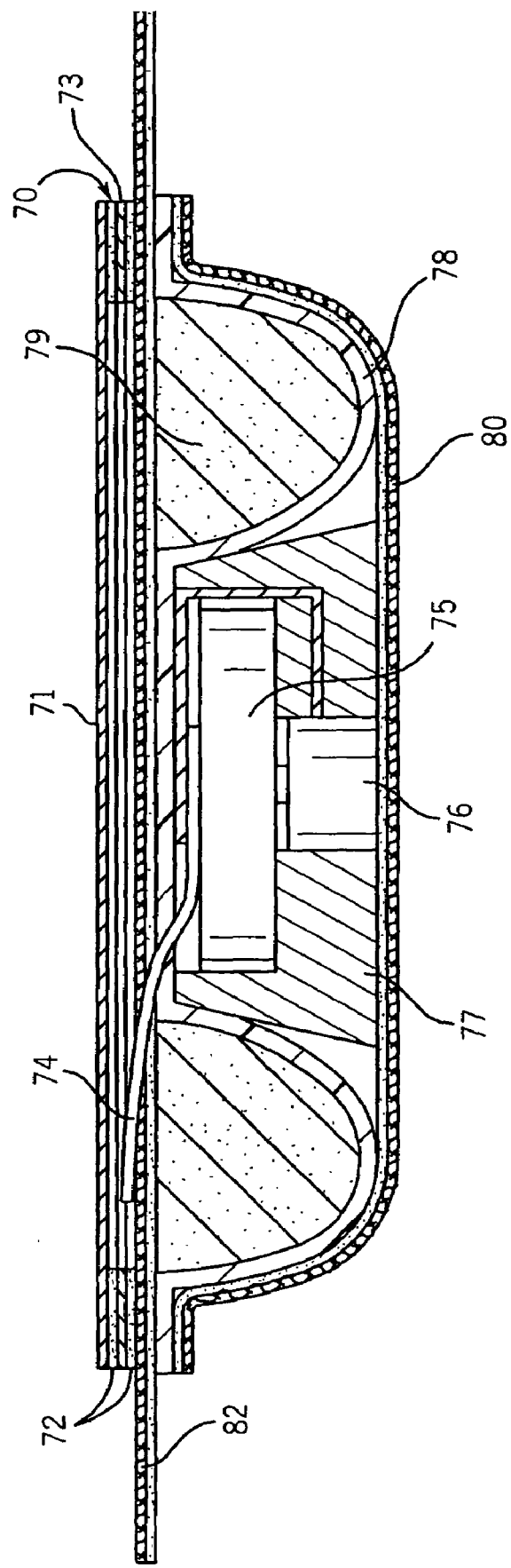
FIG. 6 is a sectional view, similar to FIG. 3, but of yet another alternative therapy patch.

Referring next to FIG. 6, there can be a peel-off structure 70 which may have an upper foil oxygen barrier 71, two layers of double-sided adhesive 72 and a release paper 73. When it is desired to start the device the peel-off structure 70 can be removed from the remainder of the device as a unit. This will expose a pull tab 74. When the tab is pulled out, that allows a contact from the motor to flex down against the battery, thereby creating an electrical circuit between the battery 75 and a motor 76.

The motor is housed in a resin 77, which also houses the battery 75. There is also a shell 78 made of a material such as a PVC casing. In that casing is positioned the iron mixture 79 previously described. There is also a lower casing 80.

When the peel-off structure 70 is removed, that exposes an adhesive bandage layer 82 which not only permits oxygen to reach the iron mixture, it also serves as a sticky adhesive bandage material that can contact the human surface that the device is to be applied on. Hence, in this device the initiator is on the same side as the adhesive (contrary to the FIG. 3 embodiment where they are on opposed sides of the device).

Figure 7A:
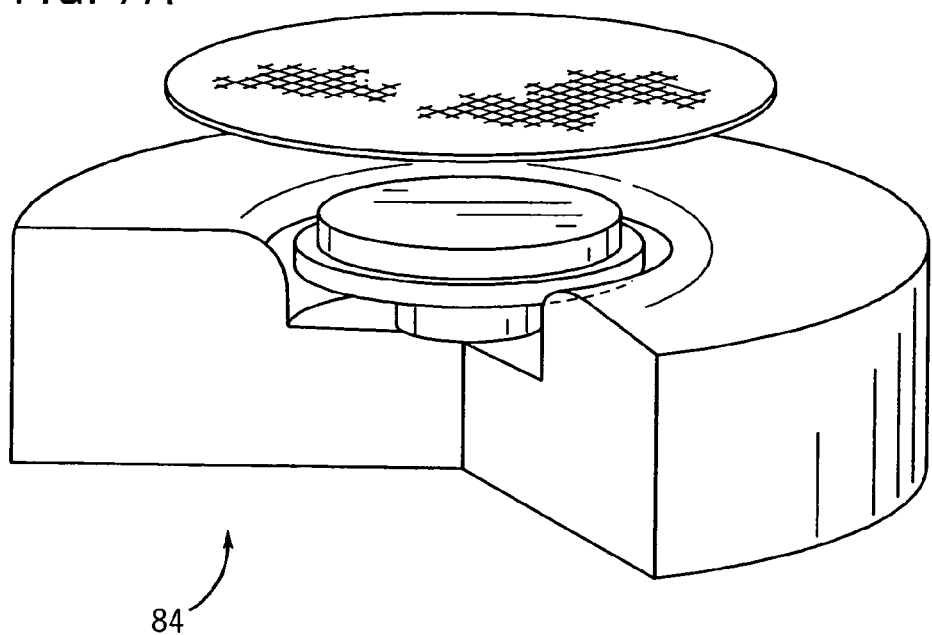
FIG. 7A is a perspective view of one motor useful in accordance with the present invention.

FIG. 7A shows a modified motor with a portion broken away for ease of illustration. In this embodiment the battery is shown above the motor.

Figure 7B:
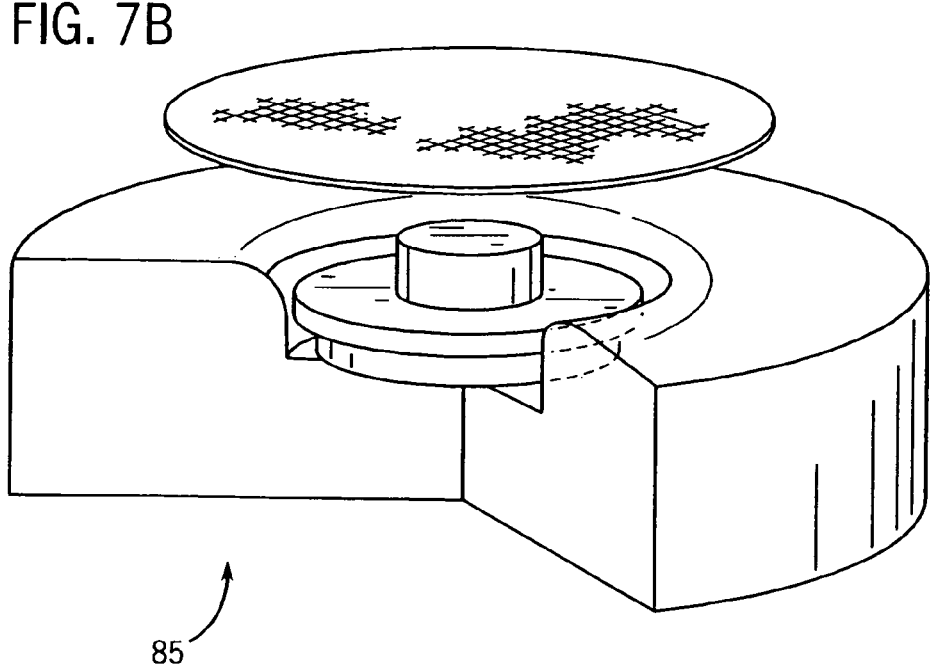
FIG. 7B is a perspective view similar to FIG. 7A, but of yet another alternative motor.

In the FIG. 7B embodiment 85 the battery is shown as positioned below the motor. With such an embodiment the upper surface of the motor can be exposed to a depression panel on the top of the puck, thereby permitting pressure to initiate the motor.

Figure 7C:
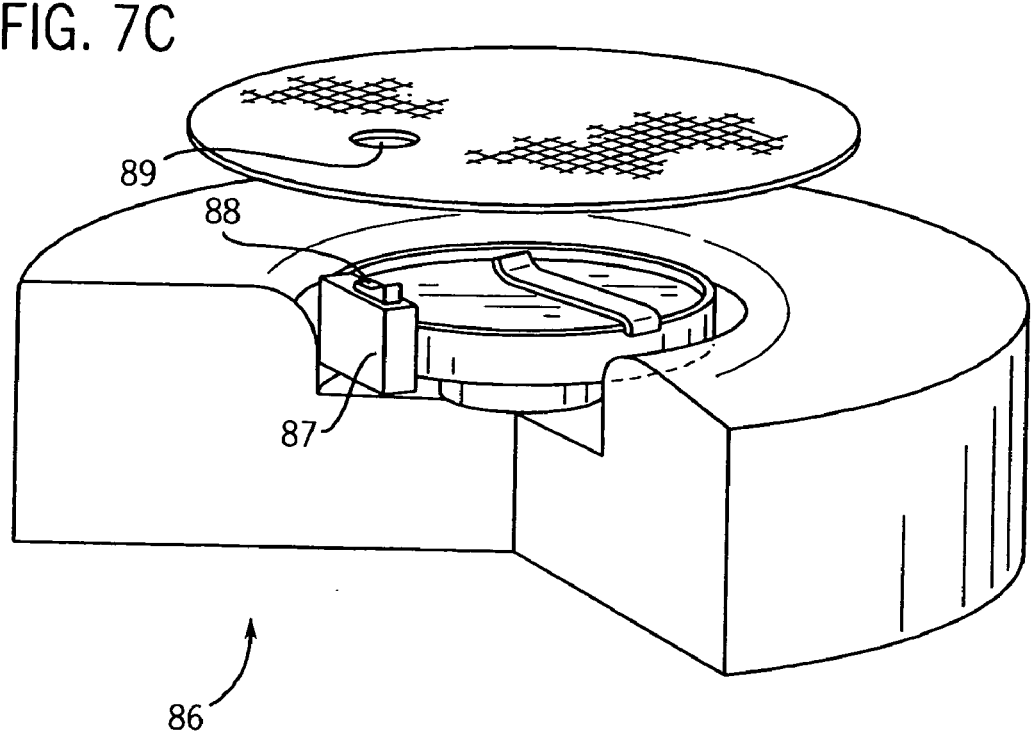
FIG. 7C is a perspective view similar to FIG. 7A, but of yet another alternative motor.

FIG. 7C shows another preferred motor 86 having a switch 87 with an on/off feature 88 that can be accessed through hole 89.

Figure 8:
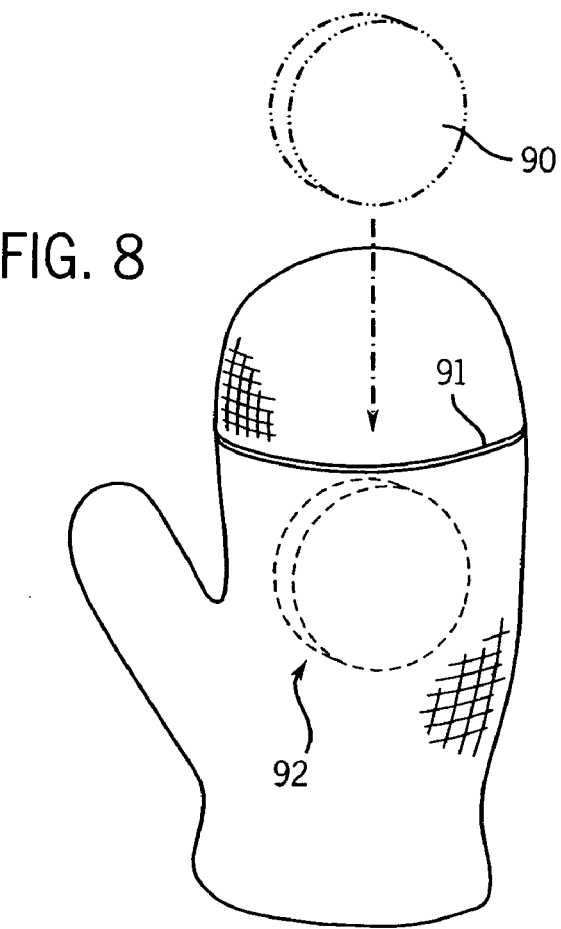
FIG. 8 is a frontal perspective view of a mitten constructed as a therapy patch.

Referring next to FIG. 8, the patch 90 is designed so as to be receivable in a cavity 91 of glove 92. Hence, instead of the patch being adhered to the skin directly, it can be used as a heated massager through the wall of the glove.

If a sodium acetate system is used instead of the iron powder based system, it is preferred for the pouch to have an over-center bi-stable (or monostable) initiator disc. When a user pops the initiator disc over center, a force is applied to the gel that begins an exothermic crystallization reaction.

The exact forms of the motor and battery are not critical. Examples of a preferred motor and a preferred battery are the Sanko 1E120 motor from Sanko Electric Co., Ltd., of Taiwan, and the Energizer CR2430 battery from Energizer Holdings, Inc.

The therapy patch 20 could include additional features. For example, a suitable portion of the therapy patch 20 can be treated with a volatile scented material, for example such as lavender or peppermint oil, that would be released upon use of the patch, especially when the patch includes a heat-producing active. Sachets or other holders of volatile scented materials (not shown) similarly could be included on or within the therapy patch 20 for the same purpose. Additionally, any selected visible surface of the therapy patch can be treated with a material that visibly changes appearance, such as color or the like, as the patch reaches its activated temperature, thus providing an actuation cue. Suitable materials to act as an activation cue include liquid crystals or leuco dyes such as those available from Color Change Corporation.

Furthermore, any suitable music or noise maker could be incorporated in the therapy patch 20, if the delivery of sound in conjunction with the other sensations provided by the patch is desired. Also, in addition, the therapy patch 20 could be treated or combined with a menthol, mentholatum, or other treatment material that could stimulate, soothe, or otherwise affect skin sensation or treatment. For example, the adhesive layer could be impregnated with that material. When a peel-off cover exposes the adhesive/chemical layer, that layer can be adhered to the skin directly such that the impregnated chemical contacts the skin. The motor and battery can then provide the vibration. Here, in addition to actual temperature changes provided by the active in the pouch, the impregnated material may enhance the perceived effect. In this regard, mentholatum may be perceived as having a heating effect in addition to actual heat supplied from the pouch.

It will be appreciated that the exact chemistry used to achieve the temperature effect is not critical. However, systems that provide an endothermic or exothermic reaction within the patch are preferred. Also, systems that require the mixing of two separate packages are less preferred than those having a single mix of chemicals that is initiated in some way.

In any event, the broad principles of the present invention can be applied in a wide variety of other ways apart from those specifically noted herein. Still other modifications may be made without departing from the spirit and scope of the invention. Thus, the claims (rather than just the preferred embodiments) should be reviewed in order to understand the full scope of the invention.

INDUSTRIAL APPLICABILITY

The present invention provides therapy patches that can deliver heat or cold, with vibration, to human muscles and the like, as well as providing methods for using these patches.

What is claimed is:

1. A therapy patch suitable to deliver vibration, as well as a temperature selected from the group consisting of hot and cold, to a target location on an animal body, the therapy patch comprising:
   a pouch defining a cavity that has an active configured to generate through a chemical reaction the temperature upon initiation;
   a motor so associated with the pouch so as to cause the pouch to vibrate when the motor is operating; and
   means for attaching a battery to the motor;
   wherein the pouch defines a frame surrounding an essentially central mounting position and the motor is mounted at that mounting position and is framed by the pouch and chemicals in the pouch that generate the chemical reaction; and
   wherein an outer cover extends over the mounting position and is removably connected to the frame.

2. The patch of claim 1, further comprising a controller capable of causing the motor to repetitively turn on and off, and/or change motor speed, in an automated manner.

3. The patch of claim 1, further comprising a battery.

4. The patch of claim 1, wherein the frame is substantially annular and the essentially central mounting position is a recess.

5. The patch of claim 1, wherein the motor is a puck that is retained between the mounting position of the pouch and the outer cover.

6. The patch of claim 5, wherein the cover encloses an opening sized to enable removal and installation of the motor.

7. The patch of claim 1, wherein the active comprises iron powder, and the pouch has a porous side wall portion that can allow ambient air to flow to the active when the porous side wall portion is exposed to ambient air.

8. The patch of claim 7, further comprising a first strip removably covering the porous side wall portion.

9. The patch of claim 1, further comprising an adhesive layer attached to the pouch and a second strip that removably covers the adhesive layer, whereby if the second strip is removed from the adhesive layer the adhesive layer is suitable to mount the pouch against human skin.

10. The patch of claim 1, further comprising a skin interface layer connected to the pouch having a flocked exposed surface.

11. The patch of claim 1, wherein the active comprises a gel having sodium acetate.

12. The patch of claim 1, wherein the motor comprises a switch configured to be depressed to activate and deactivate the motor.

13. The patch of claim 1, further comprising a visible surface that can change color when a portion of the patch changes from a first temperature to a second temperature.

14. The patch of claim 1, wherein the patch, when in use, also provides to the user one or more additional sensory effects selected from the group consisting of sound, scent, and skin sensations induced by treatment materials that stimulate, soothe, or otherwise affect skin sensation or treatment.

15. A therapy patch suitable to deliver vibration, as well as a temperature selected from the group consisting of hot and cold, to a target location on an animal body, the therapy patch comprising:
   a pouch defining a cavity that has an active configured to chemically generate the temperature upon initiation;
   a motor so associated with the pouch so as to cause the pouch to vibrate when the motor is operating; and means for attaching a battery to the motor;

wherein the motor comprises a pair of exposed electrical terminals separated by a nonconductive tab, the tab being movable between a first position in which the tab separates the terminals and a second position in which the tab is removed from the terminals to bring the terminals in contact with each other and activate the motor.

16. A therapy patch suitable to deliver vibration, as well as a temperature selected from the group consisting of hot and cold, to a target location on an animal body, the therapy patch comprising:

a couch defining a cavity that has an active configured to chemically generate the temperature upon initiation;

a motor so associated with the pouch so as to cause the pouch to vibrate when the motor is operating; and means for attaching a battery to the motor; wherein the patch further comprises a temperature sensor and a controller, wherein the controller is configured to control motor operation and respond to signals from the sensor.

17. A muscle relief kit configurable to deliver vibration, as well as a temperature selected from a group consisting of hot and cold, to a target location on an animal body, the muscle relief kit comprising:

a motor capable of causing vibrations when the motor is operating;

means for attaching a battery to the motor;

a first patch; and a second patch;

wherein each patch has a pouch defining a cavity that contains an active configured to chemically generate the heat or cold upon initiation, and each patch has a mounting location for mounting the motor;

wherein the first and second patches are connectible along a linking web, and the linking web is sealed such that even after the first and second patches are separated by tearing or otherwise cutting through the linking web, so tearing or otherwise cutting through the linking web can be achieved without exposing an interior of a pouch of a patch to ambient air.

18. A muscle relief kit configurable to deliver vibration, as well as a temperature selected from a group consisting of hot and cold, to a target location on an animal body, the muscle relief kit comprising:

a motor capable of causing vibrations when the motor is operating;

means for attaching a battery to the motor;

a first patch; and a second patch;

wherein each patch has a pouch defining a cavity that contains an active configured to chemically generate the heat or cold upon initiation, and each patch has a mounting location for mounting the motor;

wherein the first and second patches are linked together, there are at least two such motors, one of said motors is mounted to the first patch, another of said motors is mounted to the second patch, and the two motors are independently operable by a controller.

19. A therapy patch suitable to deliver vibration, as well as a temperature selected from the group consisting of hot and cold, to a target location on an animal body, the therapy patch comprising:

a pouch defining a cavity that has an active configured to chemically generate the temperature upon initiation;

a motor mounted against an outer surface of the pouch and so associated with the pouch so as to cause the pouch to vibrate when the motor is operating; and means for attaching a battery to the motor;

wherein the patch further comprises a spring arm linked to the pouch to clamp the motor against the outer surface.

* * * * *